United States Patent [19]

Pennig

[11] Patent Number: 5,346,496
[45] Date of Patent: Sep. 13, 1994

[54] DRILL-DEVICE FOR ALIGNMENT OF A BONE SCREW DRIVEN INTO THE NECK OF A FEMUR

[76] Inventor: Dietmar Pennig, Hans-Driesch-Strasse 12, 935 Köln, Fed. Rep. of Germany

[21] Appl. No.: 106,223

[22] Filed: Aug. 13, 1993

[30] Foreign Application Priority Data

Dec. 13, 1991 [DE] Fed. Rep. of Germany ....... 4141153

[51] Int. Cl.$^5$ ............................................. A61B 17/56
[52] U.S. Cl. .................................................... 606/96
[58] Field of Search .................. 606/87, 96, 98, 89, 606/80, 67, 64

[56] References Cited

U.S. PATENT DOCUMENTS

| | | | |
|---|---|---|---|
| 4,622,959 | 11/1986 | Marcus | 606/98 |
| 4,733,654 | 3/1988 | Marino | 606/80 |
| 4,865,025 | 9/1989 | Buzzi et al. | 606/96 |
| 4,881,535 | 11/1989 | Sohngen | 606/98 |

FOREIGN PATENT DOCUMENTS

| | | | |
|---|---|---|---|
| 0514662 | 11/1992 | European Pat. Off. | |
| 221356 | 4/1985 | Fed. Rep. of Germany | 606/98 |
| 668692 | 1/1989 | Switzerland | 606/96 |

*Primary Examiner*—Tamara L. Graysay
*Attorney, Agent, or Firm*—Hopgood, Calimafde, Kalil & Judlowe

[57] ABSTRACT

A drill-guide device is for use in establishing alignments for bone screws driven into the neck of a femur, for bone immobilization following a femoral-neck fracture, particularly in the circumstance of an intramedullary nail already installed in the shaft of the same femur. The device provides a drill template with at least one pair of horizontally spaced guide bores, which are sufficiently spaced to straddle opposite sides of the intramedullary nail and which can be oriented to produce drilled holes which pass up the femoral neck and into the head of a the femur. The axes of the guide bores converge to a point of their geometric intersection beyond the femoral head. Provision is made for detachably connecting the template to the proximal end of the intramedullary nail and for releasably fixing the vertical position and the elevationally tilted position of the template, for a range of adjustments to adapt the device to the differing sizes and proportions of individual patients.

13 Claims, 1 Drawing Sheet

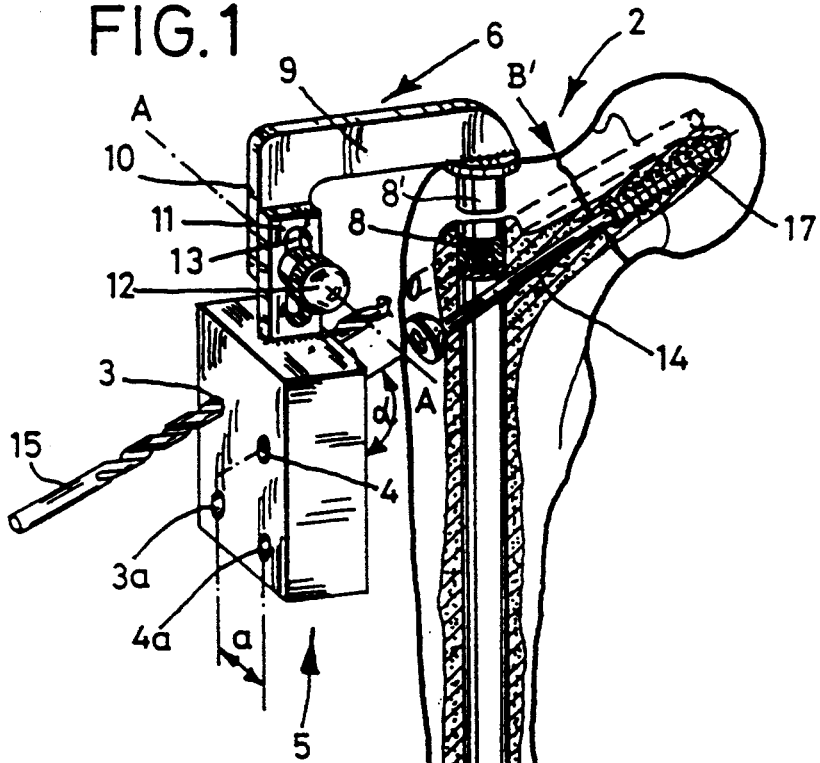
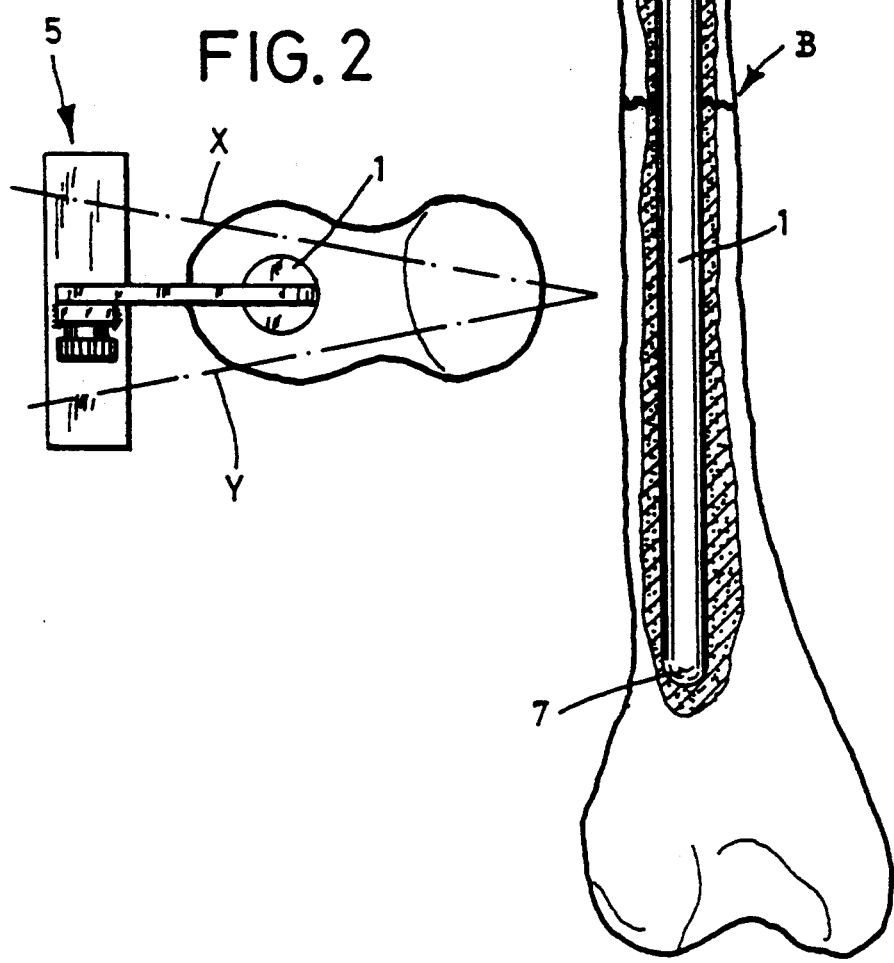

DRILL-DEVICE FOR ALIGNMENT OF A BONE SCREW DRIVEN INTO THE NECK OF A FEMUR

BACKGROUND OF THE INVENTION

The invention relates to a drill-guide device, for use in establishing alignments for bone screws driven into the neck of a femur. The device has particular application to the repair of a petrochanteric fracture of the neck of a femur, as when installing a reinforcing side plate of the nature described in my copending patent application Ser. No. 08/075,495, filed Jun. 8, 1993.

A guide device for drilling into the neck of a femur is known from U.S. Pat. No. 4,733,654, which discloses a drill template adapted to be placed on a proximal-end part of an intramedullary nail; the device is completely rigid, so that neither turning nor swinging movements are possible. Therefore, the alignment of holes to be drilled is determined once and for all, and adaptation to different conditions of an individual person are not possible.

BRIEF STATEMENT OF THE INVENTION

The primary object of the invention is to provide an improvement in a drill-guide device of the character indicated such that, in the event of a fractured femur in which an intramedullary nail has been installed, a fractured femoral neck can be set without the need to align drilled holes with holes in the intramedullary nail.

More specifically, it is an object to meet the above object with a drill-guide device which does not require traversal of the intramedullary nail and which is adaptable to a range of sizes and proportions of one to the next individual-patient use.

The invention achieves the foregoing objects by providing a drill guide (a) which has provision for attachment to the proximal end of an installed intramedullary nail, (b) which has further provision for selective axially offsetting adjustment in the distal direction, and (c) which has at least one pair of horizontally spaced guide bores that are sufficiently spaced to permit bone-screw alignments that extend into the femoral neck via passage on opposite lateral sides of the intramedullary nail.

Stated in other words, the invention provides an auxiliary attachment whereby the proximal end of the intramedullary nail can stabilize mounting of a guide fitting or jig, the latter being so devised that jig bores are aligned for drill guidance on opposite sides of the intramedullary nail and in the direction of the femoral neck or femoral head, thus permitting bone screws to thread through the shaft of the femur and into the femoral neck without interference with the installed intramedullary nail.

The jig or targeting device of the invention comprises a drill template in which there are at least two drill bores arranged alongside of each other transverse to the longitudinal axis of the intramedullary nail, and these guide bores have substantially the same slope with respect to the longitudinal axis of the intramedullary nail as the axis of the femoral neck has with respect to the axis of the femur, i.e., about 130°. However, the respective axes of these two guide bores define a single plane having the said slope of about 130°, i.e., in the direction of the sloped alignment of the femoral neck, and these guide-bore axes converge to a location of their geometric intersection, beyond the femoral head. In this connection, the guide bores are sufficiently spaced, i.e., at such separation from each other, and on alignments on opposite sides of the longitudinal axis of the intramedullary nail, that inserted drills, and thereafter inserted bone screws, thread past the installed intramedullary nail without any problem.

The drill template is adjustably carried by a suspension bar which is angularly adjustable about the intramedullary nail at its end connection to the proximal end of the intramedullary nail; at its other end, the suspension bar has vertically adjustable connection to the drill template, the vertical adjustment providing selective positioning of the template in the direction of the longitudinal axis of the intramedullary nail. Thus, the drill template is selectively positionable both angularly about the axis of the intramedullary nail and vertically, parallel to the axis of the intramedullary nail. Moreover, the suspension of the template has further provision for a range of tilt adjustment, whereby to adapt the upward slope of the drill-guide bores in the template, to the slope of an individual's femoral neck with respect to the intramedullary nail.

After insertion of bone screws which thread through the fracture of the neck of the femur, the suspension bar and its template can be removed, and the threaded formation then exposed at the proximal end of the intramedullary nail can be suitably plugged or capped.

DETAILED DESCRIPTION

A preferred embodiment of the invention will be described in detail, in conjunction with the accompanying drawings, in which:

FIG. 1 is a simplified view in perspective, diagrammatically and in partial section, to show a femur bone containing an intramedullary nail and an applied drill template of the invention; and FIG. 2 is a plan view of the diagram of FIG. 1, to enable a clear showing of the convergent relation of the axes of drill-guide bores of the drill template.

In FIG. 1 of the drawings, a femoral fracture at B has been immobilized by an installed intramedullary nail 1, and there is a further fracture B' in the femoral neck, to be immobilized despite the installed presence of the intramedullary nail 1. To immobilize the femoral neck and set its fracture B', bone screws (as at 14) must be driven through the femur, up the femoral neck and into the head of the femur.

At its proximal end, generally designated 2, the intramedullary nail 1 is provided with a threaded attachment 8 to which a correspondingly threaded rotatable element 8' of a suspension bar 6 can be engaged; the suspension bar 6 is then carried by the proximal end 2 of the intramedullary nail 1, with at least some provision for selective angular positioning of bar 6 about the axis of the intramedullary nail.

In the present description, the expression "vertical" will be understood to refer to a direction which is parallel to the longitudinal axis of the intramedullary nail 1, and the expression "horizontal" will be understood to refer to a direction which is transverse to the longitudinal axis of the intramedullary nail 1. The expression "horizontal" will sometimes also refer to a direction transverse to the direction of the femoral neck.

The suspension bar 6 is seen to comprise an angled part having two legs 9 and 10. The leg 9 is generally horizontal, having the threaded means 8, 8' at one end for removable attachment to the proximal end of the intramedullary nail 1; leg 9 extends straight and radially of the axis of the intramedullary nail and, as seen in FIG. 2, is selectively angularly adjustable for positioning in the direction of the femoral neck. The leg 10 of bar 6 is directed vertically downward, substantially parallel to the intramedullary nail 1. A drill template or jig 5 is equipped with a suspension arm 11 having an elongate slot 13 whereby a bolt 12 engaged to leg 10 and passing through slot 13 may serve to releasably clamp the template 5 in a selected vertical position with respect to bar 6, the vertical adjustability being parallel to the axis of the intramedullary nail and appropriate to the size and proportions of the involved fractured femur. The bolt 12 is also seen in FIG. 1 to be threaded to leg 10 on a horizontal axis A—A, whereby a range of angular tilting adjustment about axis A—A is also available, for adaptation of template positioning to the size and proportions of the involved femur. This relation of bolt 12 to slot 13, with its offer of vertical adjustability and adjustable angular tilting about axis A—A may be referred to as adjustable means for vertically adjusting the template in the direction parallel to the intramedullary nail and/or for adjustably tilting the template about the horizontal axis (A—A).

The drill template 5 is seen in FIGS. 1 and 2 to be provided with at least one pair of drill-guide bores 3, 4 on axes X, Y, (a) which are horizontally spaced, (b) which converge to a point of their geometric intersection beyond the femoral head and which together define a geometric plane which (c) slopes upwardly from the horizontal and which in FIG. 1 is identified as the angle α with respect to the vertical direction. This angle α is suitably and preferably about 130° and, as noted above, can be adjustably set above or below this value, to accord with the slope of the particular involved femoral neck to be immobilized.

The drill-guide bores 3, 4 are shown as the first of two pairs of drill-guide bores in template 5, the second pair (3a, 4a) being shown vertically spaced below the first pair 3, 4; both pairs (3, 4 and 3a, 4a) are transversely or horizontally spaced to the extent a at the outer face of template 5. And from FIG. 2, it will be understood that the convergent relation expressed above for axes X, Y of guide bores 3, 4 also applies for the guide bores 3a, 4a, although the upward slope α described for the geometric plane established by axes X, Y of guide bores 3, 4 may or may not be the same for the geometric plane established by the convergent axes of guide bores 3a, 4a; in fact, as set forth in greater detail in said copending patent application Ser. No. 08/075,495, the slope α for the geometric plane established by the axes of drill-guide bores 3a, 4a may be more nearly 90°, i.e., essentially horizontal, for direct adjuvant anchorage to the main shaft of the femur. In general, it is to be understood that the transverse or horizontal spacings between guide bores of each pair are in excess of the diameter of the intramedullary nail, to the extent of at least the diameter of a drill-guide bore so that bone screws, at least via the bone-screw pilot holes drilled via guide bores 3, 4, can pass into threaded engagement with the femoral head. Illustratively, FIG. 1 schematically shows a drill bit 15 guided by template bore 3 in the X-axis direction to the femoral head, and a bone screw 14 having threads 17 engaged within the femoral head has been set via the drilled hole guided by template bore 4 on the axis Y; the spacing a is such that both the drill bit 15 and the driven bone screw 14 pass through the femur and into the femoral neck without interference with the installed intramedullary nail.

After the drill jig 5 and its supporting structure, including arm 6 have served their purpose and bone screws (as at 14) have been installed, the drill jig, its supporting structure and rotatable element 8' can be removed, and the threaded formation then exposed at the proximal end of the intramedullary nail can be suitably plugged or capped for closure of said proximal end.

What is claimed is:

1. A drill-guide device for a drill to produce a bone-screw pilot hole extending substantially transverse to a longitudinally extending intramedullary nail which has been longitudinally installed in a femur having a fracture in the femoral neck thereof, wherein the intramedullary nail has a longitudinal axis and an exposed proximal end, said device comprising a drill template (5) and adjustable means for removably attaching of said template to the proximal end (2) of the intramedullary nail (1), and for adjustably tilting said template about a horizontal axis (A—A) extending transverse to the longitudinal axis of the intramedullary nail (1) and transverse to the radial direction of the femoral neck, said adjustable means including means for vertically adjusting said template in a direction parallel to the longitudinal axis of the intramedullary nail (1), said drill template (5) having at least two drill-guide bores (3, 4) which are at a horizontal spacing transverse to the longitudinal axis of the intramedullary nail (1) and transverse to the direction of the femoral neck, said spacing being sufficient for said bores to straddle the intramedullary nail (1).

2. A drill-guide device according to claim 1, in which the drill template (5) is a block and the drill-guide bores (3, 4) are on axes which define a geometric plane that is inclined above the horizontal, extending generally transverse to the intramedullary nail (1), wherein the inclination substantially conforms to the slope of the femoral neck with respect to the shaft of the femur.

3. A drill-guide device according to claim 1, in which said adjustable means for removably attaching said template to said nail comprises a suspension bar (6) removably connected to the proximal end of the intramedullary nail (1) and rotatable about the longitudinal axis of the intramedullary nail, said suspension bar extending radially outward of the intramedullary nail and having a free end, and said free end carrying said means for vertically adjustable positioning of the template (5) parallel to the longitudinal axis of the intramedullary nail (1).

4. A drill-guide device according to claim 3, in which the drill template (5) is selectively adjustable with respect to the intramedullary nail and the suspension bar (6) about said horizontal axis (A—A) transverse to the longitudinal axis of the intramedullary nail (1) and transverse to the direction of the femoral neck.

5. A drill-guide device according to claim 3, in which the means for removable attachment includes threaded attachment means (8) at the proximal end of the intramedullary nail (1) and at an end of the suspension bar (6).

6. A drill-guide device according to claim 5, in which the threaded attachment means at the proximal end of the intramedullary nail (1) is adapted for closure after the threaded attachment means at the end of the suspension bar has been removably disconnected.

7. A drill-guide device according to claim 1, in which said drill-guide bores are part of a greater plurality of drill-guide bores (3, 3a; 4, 4a), said plurality of drill-guide bores being arranged one vertically below the other in transversely spaced vertical planes parallel to the longitudinal axis of the intramedullary nail (1).

8. A drill-guide device according to claim 1, in which said at least two drill-guide bores define a horizontally spaced pair which is one of a plurality of vertically spaced pairs of drill-guide bores, wherein corresponding bores of each pair are aligned in first and second vertical planes having said horizontal spacing.

9. A drill-guide device for a drill to produce a bone-screw pilot hole extending substantially transverse to a longitudinally extending intramedullary nail which has been longitudinally installed in a femur having a fracture in the femoral neck thereof, wherein the intramedullary nail has an exposed proximal end, said device comprising a drill template (5) and adjustable means for removably attaching said template to the proximal end (2) of the intramedullary nail (1) and for adjustably tilting said template about a horizontal axis (A—A) extending transverse to the longitudinal axis of the intramedullary nail (1) and transverse to the direction of the femoral neck, said adjustable means including means for vertically adjusting said template in a direction parallel to the longitudinal axis of the intramedullary nail (1), said drill template (5) being a block having at least two drill-guide bores (3, 4) which are at a horizontal spacing (a) transverse to the longitudinal axis of the intramedullary nail (1) and transverse to the direction of the femoral neck, said spacing being sufficient for said bores to straddle the intramedullary nail (1), said drill-guide bores (3,4) being on axes (X, Y) which define a geometric plane that is inclined in substantial conformance with the slope of the femoral neck with respect to the shaft of the femur, the axes (X, Y) of the respective drill-guide bores (3, 4) converging in the direction of the alignment of the femoral neck in such manner that these axes geometrically intersect beyond the femoral head.

10. A drill-guide device according to claim 9, in which said drill-guide bores (3, 4) constitute a first pair of a plurality of pairs of drill-guide bores (3, 4; 3a, 4a), said pairs being vertically spaced from each other and similarly convergent.

11. A drill-guide device according to claim 10, in which the respective axes of the drill-guide bores of at least a second pair of said plurality define a geometric plane which is at an angle other than the slope of said first pair with respect to the longitudinal axis of the intramedullary nail.

12. A drill-guide device for a drill to produce one or more bone-screw pilot holes for bone-screw stabilization of a femoral-neck fracture, particularly in the circumstance of an intramedullary nail already installed in the shaft of the same femur, the intramedullary nail having a longitudinal axis and an exposed proximal end, said device comprising a drill template and a suspension system with means for removably and rotatably connecting said template to the proximal end of the intramedullary nail, said suspension system comprising a straight member extending radially with respect to said axis and rotatable about said axis at the connection to the intramedullary nail and therefore providing a means of visually positioning said straight member for viewed registration with the radial direction of the femoral neck, a vertically downward member connected to said straight member and including means providing vertically adjustable and releasable clamped connection to said template, said template having at least one pair of horizontally spaced drill-guide bores which are spaced sufficiently to straddle opposite sides of the intramedullary nail and which can be oriented for the guided drilling of holes which traverse but do not interfere with opposite sides of the femoral shaft and which extend up the femoral neck and into the head of the femur, the axes of the respective guide bores converging to their geometric intersection at a point which is beyond the femoral head.

13. A drill-guide device according to claim 12, in which said means providing the releasable clamped connection includes means providing a range of selectively variable tilting adjustment about a horizontal axis, whereby to permit the device to be set for adaptation to the particular slope of an individual's femoral-neck direction with respect to the installed intramedullary nail.

* * * * *